US00PP35620P2

(12) United States Plant Patent
Flore

(10) Patent No.: US PP35,620 P2
(45) Date of Patent: Jan. 30, 2024

(54) ***PHALAENOPSIS* PLANT NAMED 'MI01764'**

(50) Latin Name: *Phalaenopsis hybrida*
Varietal Denomination: MI01764

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 18/214,278

(22) Filed: Jun. 26, 2023

Related U.S. Application Data

(60) Provisional application No. 63/356,011, filed on Jun. 27, 2022.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Karen M Redden
(74) *Attorney, Agent, or Firm* — C. Anne Whealy

(57) ABSTRACT

A new and distinct cultivar of *Phalaenopsis* plant named 'MI01764', characterized by its upright plant habit; vigorous growth habit and rapid growth rate; strong and flexible flowering stems; outwardly arching leaves; freely flowering habit with typically two inflorescences per plant, each inflorescence with numerous flowers; dark purple-colored flowers with white-colored margins; and good postproduction longevity.

1 Drawing Sheet

Figure 1:
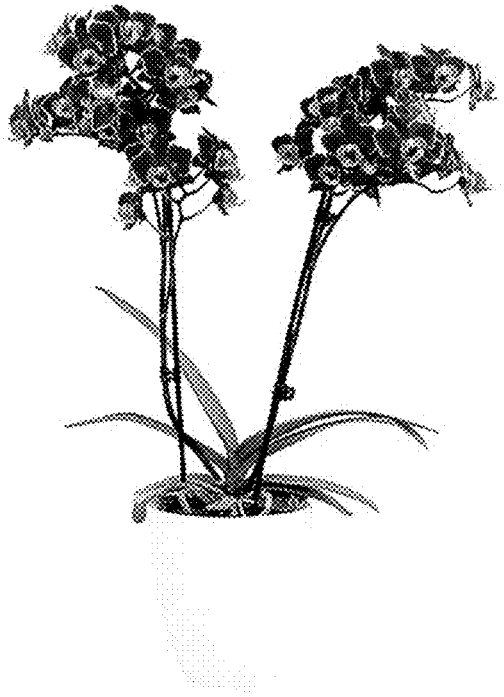

Botanical designation: *Phalaenopsis hybrida.*
Cultivar denomination: 'MI01764'.

An European Community Plant Breeder's Rights application for the instant plant was filed by the Applicant/Assignee of the instant application, Microflor N.V. of Lochristi, Belgium on Mar. 25, 2022, application number 2022/0780. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'MI01764'.

The new *Phalaenopsis* plant is a product of a planned breeding program conducted by the Inventor in Lochristi, Belgium. The objective of the breeding program is to develop new freely flowering *Phalaenopsis* plants with good leaf shape and relatively large flowers with unique and attractive flower coloration.

The new *Phalaenopsis* plant originated from a cross-pollination by the Inventor in April, 2014 in Lochristi, Belgium of a proprietary selection of *Phalaenopsis hybrida* identified as code number PHM00312, not patented, as the female, or seed, parent with a proprietary selection of *Phalaenopsis hybrida* identified as code number PHM00345, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in December, 2016.

Asexual reproduction of the new *Phalaenopsis* plant by in vitro meristem propagation in a controlled environment in Lochristi, Belgium since April, 2018 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI01764'. These characteristics in combination distinguish 'MI01764' as a new and distinct *Phalaenopsis* plant:

1. Upright plant habit.
2. Vigorous growth habit and rapid growth rate.
3. Strong and flexible flowering sterns.
4. Outwardly arching leaves.
5. Freely flowering habit with typically two inflorescences per plant, each inflorescence with numerous flowers.
6. Dark purple-colored flowers with white-colored margins.
7. Good postproduction longevity.

Plants of the new *Phalaenopsis* can be compared to plants of the female parent selection. Plants of the new *Phalaenopsis* differ primarily from plants of the female parent selection in the following characteristics:

1. Plants of the new *Phalaenopsis* are taller than and not as compact as plants of the female parent selection.
2. Flowers of plants of the new *Phalaenopsis* are dark purple in color with white-colored margins whereas flowers of plants of the female parent selection are purplish pink in color with white-colored margins.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* have smaller flowers than plants of the male parent selection.
2. Flowers of plants of the new *Phalaenopsis* are dark purple in color with white-colored margins whereas flowers of plants of the male parent selection are white in color with reddish purple-colored spots.

Plants of the new *Phalaenopsis* can be compared to plants of *Phalaenopsis hybrida* 'Cha-Cha', not patented. In side-by-side comparisons, plants of the new *Phalaenopsis* differ primarily from plants of 'Cha-Cha' in the following characteristics:

1. Flowers of plants of the new *Phalaenopsis* do not have stripes whereas flowers of plants of 'Cha-Cha' are striped.
2. Lateral sepals of flowers of plants of the new *Phalaenopsis* are ovate to lanceolate and asymmetrical in shape whereas lateral sepals of flowers of plants of 'Cha-Cha' are elliptical and symmetrical in shape.
3. Cirrhose tips of flowers of plants of the new *Phalaenopsis* are longer than cirrhose tips of flowers of plants of 'Cha-Cha'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph at the top of the sheet (FIG. 1) is a side perspective view of a typical flowering plant of 'MI01764' grown in a container.

Figure 2:
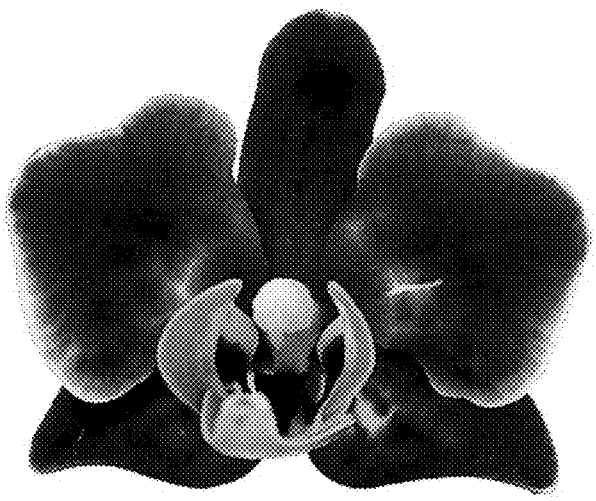

The photograph at the bottom of the sheet (FIG. 2) is a close-up view of a typical flower of 'MI01764'.

DETAILED BOTANICAL DESCRIPTION

The aforementioned photographs and following observations and measurements describe plants grown during the autumn and early winter in 9-cm containers in a glass-covered greenhouse in Lochristi, Belgium and under cultural practices typically used in commercial *Phalaenopsis* production. During the production of the plants, day and night temperatures ranged from 18 C to 29 C and light levels ranged from 150 Watt/m$^2$ to 375 Watt/m$^2$. Plants were 70 weeks old when the photographs and description were taken. In the following description, color references are made to The Royal Horticultural Society Colour Chart, 2001 Edition, except where general terms of ordinary dictionary significance are used.

Botanical classification: *Phalaenopsis hybrida* 'MI01764'.

Parentage:

*Female parent*.—Proprietary selection of *Phalaenopsis hybrida* identified as code number PHM00312, not patented.

*Male parent*.—Proprietary selection of *Phalaenopsis hybrida* identified as code number PHM00345, not patented.

Propagation:

*Type*.—By in vitro meristem propagation.

*Time to initiate roots, summer*.—About nine to ten weeks at temperatures about 26 C.

*Time to initiate roots, winter*.—About ten to eleven weeks at temperatures about 26 C.

*Time to produce a rooted young plant, summer*.—About 140 to 160 days at temperatures about 26 C.

*Time to produce a rooted young plant, winter*.—About 150 to 180 days at temperatures about 26 C.

*Root description*.—Thick, fleshy; typically grey green in color; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two inflorescences per plant, each inflorescence with numerous flowers; monopodial; vigorous growth habit and rapid growth rate.

*Plant height, substrate level to top of foliar plane*.—About 9.5 cm.

*Plant height, substrate level to top of inflorescences*.—About 41 cm.

*Plant diameter or spread*.—About 36 cm.

Leaf description:

*Arrangement and quantity*.—Distichous, simple; sessile; about seven leaves per plant.

*Length*.—About 19 cm.

*Width*.—About 7 cm.

*Aspect*.—Outwardly arching.

*Shape*.—Elliptic.

*Apex*.—Unequal obtuse.

*Base*.—Sheathing.

*Margin*.—Entire.

*Texture and luster, upper and lower surfaces*.—Smooth, glabrous; moderately glossy.

*Venation pattern*.—Camptodromous.

*Color*.—When opening, upper surface: Close to 137A. When opening, lower surface: Close to 137C. Fully expanded leaves, upper surface: Close to 137B; venation, close to 137B. Fully expanded leaves, lower surface: Close to 137C; venation, close to 137C.

Inflorescence description:

*Appearance and flowering habit*.—Showy zygomorphic flowers arranged on axillary branched racemes; typically two inflorescences per plant; each inflorescence with about 21 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 16 to 17 weeks after an inductive cooling period; flowers open about six weeks after flower buds develop.

*Flower longevity*.—Long flowering period, individual flowers maintain good substance for about ten weeks on the plant; flowers not persistent.

*Inflorescence length* (*lowermost flower to inflorescence apex*).—About 25 cm.

*Inflorescence width*.—About 18 cm.

*Flower buds*.—Height: About 1.3 cm. Diameter: About 1 cm. Shape: Ovate. Color: Close to 194C shaded with close to 187A and venation, close to 187A.

*Flower diameter*.—About 5 cm.

*Flower depth*.—About 2.1 cm.

*Petals, quantity and arrangement*.—Three, two lateral petals and one center petal transformed into a labellum.

*Lateral petals*.—Length: About 2.4 cm. Width: About 2.6 cm. Shape: Trullate to deltoid. Apex: Rounded. Margin: Entire to slightly undulate. Texture and luster, upper and lower surfaces: Smooth, glabrous, velvety; matte. Color: When opening and fully opened, upper surface: Close to 187A; towards the margins, close to 155D; color does not change with subsequent development. When opening and fully opened, lower surface: Close to 77A; towards the center, close to 155D; color does not change with subsequent development.

*Labella*.—Appearance: Tri-lobed with two lateral lobes and a central lobe. Length: About 2 cm. Width: About 1.3 cm. Shape, lateral lobes: Obovate. Shape, central lobe: Trullate. Apex, lateral lobes: Obtuse. Apex, central lobe: Slightly cleft with two short, narrow and recurved cirrhose tips. Margins, lateral and central lobes: Entire. Texture and luster, upper and lower surfaces: Smooth, glabrous, moderately velvety; matte. Callosities: Located at the base of the labellum and attachment point of the lateral petals; about 3 mm in length, about 3 mm in width and about 4 mm in height. Color: When opening and fully opened, upper surface: Lateral lobes: Close to 155D; large spot near base, close to 187A; smaller spots in the center, close to 187A; and smaller spots towards the apex, close to 78B. Central lobe: Center, close to 155D; towards the base, close to 78B; spots, close to 187B. Callosities: Close to 187A. When opening and fully opened, lower surface: Lateral and central lobes: Close to 155D with colors of the upper surface visible.

*Sepals*.—Quantity and arrangement: Three, two lower lateral sepals and one upper dorsal sepal. Length, lateral sepal: About 2.7 cm. Width, lateral sepals: About 2.7 cm. Length, dorsal sepal: About 1.6 cm. Width, dorsal sepal: About 1.3 cm. Shape, lateral sepals: Ovate to lanceolate; asymmetrical. Shape, dorsal sepal: Narrowly elliptic. Apex, lateral sepals: Bluntly acute. Apex, dorsal sepal: Obtuse. Base, lateral and dorsal sepals: Obtuse. Margin, lateral and dorsal sepals: Entire. Texture and luster, lateral and dorsal sepals, upper and lower surfaces: Smooth, glabrous, velvety; matte. Color, lateral and dorsal sepals: When opening and fully opened, upper surface: Close to 187A. When opening and fully opened, lower surface: Close to 77A; center, close to 155D; venation, close to 77A.

*Peduncles*.—Length: About 41 cm. Diameter: About 5 mm. Strength: Strong, somewhat flexible. Aspect: Initially about 65 degrees from horizontal to mostly upright with development. Texture and luster: Smooth, glabrous; matte. Color: Close to 200A.

*Pedicels*.—Length: About 4 cm. Diameter: About 3 mm. Strength: Moderately strong. Aspect: About 90 degrees from peduncle axis. Texture and luster: Smooth, glabrous; matte. Color: Proximally, close to 187A and distally, close to 145C.

*Reproductive organs*.—Androecium: Column length: About 9 mm. Column width: About 5 mm to 6 mm. Column color: Close to 155D slightly blushed with close to 78B. Pollinia quantity: Two. Pollinia diameter (per two pollinia): About 3 mm. Pollinia color: Close to 25B. Gynoecium: Stigma length: About 4 mm. Stigma width: About 4.5 mm. Stigma shape: Broadly rhombic. Stigma color: Close to 155D. Ovary length: About 1.5 cm. Ovary diameter: About 2 mm. Ovary color: Close to 145C; distally, slightly blushed with close to 80C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15 C to about 40 C.

It is claimed:

1. A new and distinct *Phalaenopsis* plant named 'MI01764' as illustrated and described.

* * * * *